United States Patent
Ivanov et al.

(10) Patent No.: US 11,857,291 B2
(45) Date of Patent: Jan. 2, 2024

(54) SERIAL ARCHITECTURE AND ENERGY SAVING METHODS FOR ULTRASOUND AND THERMOACOUSTIC SYSTEMS

(71) Applicant: PhotoSound Technologies, Inc., Houston, TX (US)

(72) Inventors: Vassili Ivanov, Houston, TX (US); Sergey A. Ermilov, Houston, TX (US)

(73) Assignee: PhotoSound Technologies Inc., Houston, TX (US)

( * ) Notice: Subject to any disclaimer, the term of this patent is extended or adjusted under 35 U.S.C. 154(b) by 40 days.

(21) Appl. No.: 16/930,876

(22) Filed: Jul. 16, 2020

(65) Prior Publication Data
US 2022/0015642 A1    Jan. 20, 2022

(51) Int. Cl.
| | | |
|---|---|---|
| A61B 5/00 | (2006.01) | |
| A61B 8/00 | (2006.01) | |
| A61B 90/00 | (2016.01) | |
| A61B 8/08 | (2006.01) | |

(52) U.S. Cl.
CPC .......... *A61B 5/0095* (2013.01); *A61B 8/4416* (2013.01); *A61B 8/5261* (2013.01); *A61B 8/56* (2013.01); *A61B 90/37* (2016.02); *A61B 5/0035* (2013.01); *A61B 2090/378* (2016.02)

(58) Field of Classification Search
CPC .......... A61B 5/0095; A61B 2560/0209; A61B 90/37; A61B 8/56; A61B 2090/378; A61B 5/0035; A61B 5/5655
See application file for complete search history.

(56) References Cited

U.S. PATENT DOCUMENTS

| | | | | |
|---|---|---|---|---|
| 2011/0066023 A1* | 3/2011 | Kanayama | ......... | G01N 29/0609 600/407 |
| 2014/0031694 A1* | 1/2014 | Solek | ................... | B06B 1/0622 600/459 |
| 2014/0039293 A1* | 2/2014 | Oraevsky | ............. | A61B 5/0095 600/407 |
| 2016/0135692 A1* | 5/2016 | Lisogurski | ......... | A61B 5/02416 600/324 |
| 2016/0259035 A1* | 9/2016 | Pandey | ................ | G10K 11/346 |
| 2016/0287211 A1* | 10/2016 | DaCosta | .................. | A61B 8/48 |
| 2018/0199820 A1* | 7/2018 | Hashimoto | ............ | A61B 8/546 |

(Continued)

*Primary Examiner* — John D Li
(74) *Attorney, Agent, or Firm* — Kurtz Firm, PLLC (57) ABSTRACT

Disclosed is the electronic architecture, including component arrangement and use of switches, and power saving method for use in a dual mode USTA instrumentation. In an embodiment, the instrument architecture includes US and TA analog components, including a transducer, TA preamplifier, pulser, switches, and AFE (or ADC with programmable amplifier) arranged in a way which allows efficient usage of the same transducer elements, electronic components, wiring, and AFE channels in both US and TA modalities. The operation with fast power control over the TA preamplifier is described, which allows turning off the TA preamplifier power between TA measurements cycles with or without US measurement between TA measurements. TA preamplifier energy saving allows such designs to reduce TA preamplifier power consumption many times, which enables TA preamplifier integration inside transducer housing or probe housing, and/or the use of the TA preamplifier in portable battery-operated or hand-held devices.

16 Claims, 8 Drawing Sheets

(56) References Cited

U.S. PATENT DOCUMENTS

2018/0199821 A1\* 7/2018 Hashimoto .......... A61B 5/7225
2019/0175149 A1\* 6/2019 Dickie ................. A61B 8/4254
2021/0124044 A1\* 4/2021 Haque ................... A61B 8/488

\* cited by examiner

SERIAL ARCHITECTURE AND ENERGY SAVING METHODS FOR ULTRASOUND AND THERMOACOUSTIC SYSTEMS

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The invention generally relates to the field of biomedical (including biological, preclinical, and medical) imaging, sensing, and monitoring. Specifically, the invention relates to devices and methods that provide images and information on internal structures, molecular composition, and functional processes inside a live body based on intrinsic or induced thermoacoustic (TA) and ultrasound (US) contrast.

BACKGROUND

Thermoacoustics in Biology and Medicine

Thermoacoustics is a physical phenomenon that is manifested by conversion of electromagnetic energy absorbed by matter into broadband US waves (TA waves). Those TA waves can be measured at a single point or at multiple spatial locations by transducers with special low-noise high-sensitivity electronics, and then converted into parameters, signals or images informing on the spatial and temporal distribution of electromagnetic energy absorbed inside the matter. Optimally, those measurements should be performed by broadband devices capable of sensing TA waves with frequencies anywhere between tens of kHz and tens of MHz. Some particular types of thermoacoustics, which are used in biology and medicine include photoacoustics or optoacoustics (visible and infrared light is used for excitation), microwave acoustics (millimeter-range wavelengths of electromagnetic energy), and X-ray acoustics. Pulsed electromagnetic excitation, with individual pulse duration on the order of 1-1000 ns, is frequently used in biomedical thermoacoustics, due to its high potency for generation of a measurable TA effect in biological tissue and availability of excitation sources. Biomedical thermoacoustics is a rapidly developing field, and the prototype and commercial TA technologies continue demonstrating utility and superiority in a wide range of applications including diagnostic imaging and sensing, monitoring therapies and surgical interventions, drug development, fundamental biology and medicine.

Ultrasound in Biology and Medicine

Ultrasound is widely used in clinics and biomedical sciences in applications requiring anatomical and functional imaging, sensing and monitoring of tissues and organs, therapeutic procedures and surgery. An ultrasound instrument, as a rule, serves for both irradiation of tissue with ultrasonic waves and detection of the said ultrasonic waves after they are scattered or otherwise altered by the tissue. The frequency bandwidth in US applications is typically much narrower than that in TA applications, while the generated and measured ultrasound signals are much larger.

Ultrasound and Thermoacoustic Imaging (USTA) in Biology and Medicine

Combined dual-modality ultrasound and thermoacoustic imaging (USTA) has been proposed as a promising biomedical technology, which carries advantages of similar detection principles and instrumentation, while enhancing each one individual modality with the benefits of the other. For example, superior imaging depth and mechanical tissue contrast provided by ultrasound could be enhanced with functional and molecular imaging provided by multi-wavelength photoacoustics. The major problem preventing so far a development of an efficient, clinically acceptable and compact USTA system seems to be in a significant discrepancy of technical requirements imposed by each individual modality on the signal sensitivity, dynamic range, and frequency bandwidth, which is typically being addressed by building two stand-alone data acquisition units communicating via external control electronics.

USTA Electronic Architecture

Dual-modality USTA system architecture can be based on parallel US and TA electronic channels sharing the same or different transducer elements. This approach is used in a PhotoSound MoleculUS system as well as other USTA research and clinical systems. Energy and Electric Impedance Requirements for a USTA System TA imaging applications require transducer arrays with a large number of elements used in Rx-only mode. Electrically transducer elements are represented by capacitive sensors with element capacitance in a broad range from less than 1 pF to several nF. The lower end of this range can be exemplified by transducers used in photoacoustics and low-frequency ($\leq 1$ MHz) X-ray acoustic applications. Higher end of the range are narrow-band high frequency ultrasound transducer arrays have performance deficiencies in a TA mode. In a TA mode, each capacitive transducer channel produces low level and broad band electrical signals. Parasitic capacitance of the transmission line between the transducer element and preamplifier input produces charge redistribution over parasitic capacitance and voltage signal loss. Low level of transducer capacitance requires short-length and low-capacitance transmission line between transducer and the first amplification stage. The combination of a capacitive sensor with capacitance C and an input resistance R of the first amplification stage forms a high-pass RC filter for input signals with corner frequency $1/(2\pi RC)$. Broadband analog signal, requires a low value of this corner frequency and correspondingly a high value of the first preamplifier stage input impedance R. The high-value of preamplifier input impedance R produces impedance mismatch in the transmission line termination. Another mismatch is a capacitive transducer at the opposite end of the transmission line. Such impedance mismatches at both ends of the transmission line create ¼ wavelength resonances with first harmonic frequencies as low as 25 MHz for a two-meter-long transmission line (transducer cable). Suppression of ¼ wavelength resonances in TA applications often requires a shorter cable length. Ideally, the first preamplifier stage should be located inside the transducer array housing close to the transducer elements. The TA preamplifier has low output impedance, typically 50Ω, and is capable of driving transmission lines with matching impedance terminated with impedance-matching resistor at the device transforming analog signal to digital signal. Such device may or may not contain analog stages, like amplification stages, analog bandwidth filters, ADC drivers. Such device can be called a data acquisition system (DAQ), Analog-to-Digital Converter (ADC) or ultrasound analog front-end (AFE) end. In the following text the device will be called AFE after Texas Instruments ultrasound AFE family, for example AFE5832, AFE5816, etc. Impedance matching transmission line between a TA preamplifier output and AFE input can be as long as needed, for example 2 meters.

TA imaging applications require large number of channels equipped with TA preamplifiers resulting in relatively high-power consumption. For example, a PhotoSound Legion-series multichannel preamplifier design with discrete components has power consumption of 30 mW per channel. The power consumption of preamplifier with 256-channels excluding power supply losses is 8 W and power consumption of preamplifier with 1024-channels is about 32 W. This level of power consumption does not allow integration of a TA preamplifier inside transducer array housing, because the preamplifier-generated heat cannot be dissipated efficiently inside a small sealed volume. Power consumption is also a limiting factor for battery operated portable and handheld devices. Power consumption of the existing commercial TA preamplifiers and prototypes cannot be greatly reduced without degradation of input noise level and signal-to-noise ratio.

SUMMARY

In an embodiment, the disclosed serial architecture and methods allow provision of an instrument with dual US and TA imaging modalities with only a single modality operating at any particular time moment, which (1) incorporates and shares the components required for both modalities, (2) at each particular time moment of operation enables efficient engagement of only those components which are required for operation of an active single modality and (3) at each particular time moment of operation enables efficient exclusion (bypass) of the components which are non-essential for operation of an active single modality. The disclosed methods also allow fast energy saving mode (standby mode) when components specific for one mode are not in use, enabling reduction of heat-dissipation in the spatially confined areas of the instrument and enabling fast activation/deactivation cycles of each particular modality many times per second.

BRIEF DESCRIPTIONS OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention. The disclosed embodiments are illustrated by way of example and not limitation in the figures of the accompanying drawings in which like references indicate similar elements.

FIG. 1 shows the analog signal chain for the serial USTA system architecture.

Pulser (102) operation in TA and US Rx modes is shown in FIG. 1A (111). Pulser operation in US Tx mode is described in FIG. 1A (112).

In FIGS. 1A-1E, the top panel describes Rx only operation in TA mode. In TA mode, TA preamplifier module (104) is fully powered and inserted into Rx analog signal chain.

In FIG. 1A-1E, the bottom panels describe Tx and Rx operation in US mode. In US mode, TA preamplifier output is disconnected from the analog signal chain. In US mode, TA preamplifier (104) operates in the fast energy saving mode indicated as a shaded triangle (104). The energy saving mode is fast, if the preamplifier can enter and exit the energy saving mode on µs time scale. For example, the fast energy saving mode can be implemented in Analog Devices, Inc. ADA4895 operational amplifier IC family. ADA4895 can be disabled into the energy saving state within 0.25 µs and re-enabled back to normal operation within 6 µs according to the device datasheet.

The analog wiring is shown with lines connecting individual signal chain components. The analog wiring may be implemented via rigid or flexible PCB traces, internal routing inside ICs, connectors, and cables, including micro-coaxial cable bundles.

The analog signal path in a particular mode of operation is represented by lines with increased thickness. Direction of the signal propagation from the source to the receiver is shown using arrows with Tx and Rx signal labels. TA mode is Rx only. US mode might operate as US Tx and US Rx. Arrow direction out of the transducer corresponds to Rx signal and into the transducer to Tx signal.

The analog signal chain is shown for a single channel of a USTA system. Digital controls and components are present in addition to analog components, but are not shown except for AFE (110). The system may have multiple channels, for example, 32, 96, 256 channels or more. The serial architecture can be used with or without channel multiplexing. The channel multiplexing, including multiplexing of ADC, pulser, and other components is not shown in FIG. 1.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment, and such references mean at least one.

Reference in this specification to "an embodiment" or "the embodiment" means that a particular feature, structure, or characteristic described in connection with the embodiment is included in at least an embodiment of the disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The present invention is described below with reference to block diagrams and operational illustrations of methods and devices that provide ultrasound and thermoacoustic imaging or data generation. It is understood that each block of the block diagrams or operational illustrations, and combinations of blocks in the block diagrams or operational illustrations, may be implemented by means of analog or digital hardware and computer program instructions. These computer program instructions may be stored on computer-readable media and provided to a hard-core or soft-core processor of a general purpose computer, special purpose computer, field-programmable gate array (FPGA), ASIC, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein "another" or "other" may mean at least a second or more of the same or different elements or components thereof. The terms "comprise" and "comprising" are used in the inclusive, open sense, meaning that additional elements may be included. As used herein, the term "or" refers to "and/or" unless explicitly indicated to refer to alternatives only or the alternatives are mutually exclusive.

As used herein, the term "about" refers to a numeric value, including, for example, whole numbers, fractions, and percentages, whether or not explicitly indicated. The term "about" generally refers to a range of numerical values (e.g., ±25% of the recited value unless explicitly stated otherwise) that one of ordinary skill in the art would consider approximately equal to the recited value (e.g., having the same function or result). In some instances, the term "about" may include numerical values that are rounded to the nearest significant digit.

As used herein, the following terms and abbreviations have the following meanings:

ADC—analog to digital converter.
AFE—analog front end, integrated US amplifier and ADC or separate US amplifier and ADC.
Analog signal is an electrical signal, which value changes continuously. In the modern US and TA instrumentation with digital algorithms of image reconstruction, amplified Rx analog signal from the transducer is digitized using ADC device.
Bypass—bypassing of an analog device connected in-series in the analog signal chain is connecting short matching input(s) and output(s) together. The active device output has to be disconnected from the signal chain. In some cases, device input has to be disconnected, for example, in FIG. 1C-E TA preamplifier input is disconnected in US mode to protect TA preamplifier input from US Tx high voltage.
DAQ—data acquisition device, typically based on ADC with addition of PC interface and a (pre)amplifier or AFE.
EMI—electromagnetic interference.
FPGA—field programmable gate array IC.
Hard-core processor is a processor implemented on hardware level, such as a microprocessor or programmable microcontroller.
HV—high-voltage.
HV switch—high-voltage switch.
IC—integrated circuit with a single die or multiple dies inside packaging.
Serial USTA system architecture is the system architecture in which Rx US and TA analog signals sharing the signal path components and including the same ADC channels arranged in series for both US and TA modalities. Shared Rx path excludes components which are required in one, but not the other mode, for example, TA preamplifier is typically bypassed in US mode.
LV—low voltage.
Parallel USTA system architecture is the system architecture in which US and TA Rx analog signal split or completely separate into US and TA analog signal chains, and in which separate ADC devices are used for US and TA signals.
PC—personal computer.
PCB—printed circuit board.
Preamplifier is the first stage amplification circuit.
Rx—receive mode.
Soft-core processor is a processor implemented on firmware code level, for example MicroBlaze™ soft-core processor implemented as FPGA firmware code is available from Xilinx Inc. of San Jose, CA. Soft-core processors have functionality similar to functionality of hard-core processors.
SPST—single pole single throw. A type of electric switch with two terminals and one ON position, which can be implemented electronically or mechanically.
SPDT—single pole double throw. A type of electric switch with three terminals and two ON positions, which can be implemented electronically or mechanically.
TA—thermoacoustics, which includes optoacoustics, photoacoustics, microwave acoustics, X-ray acoustics and other thermoacoustic phenomena.
TA mode—thermoacoustic mode. TA mode is Rx-only analog circuit operation mode used for TA.
TA preamplifier is a preamplifier dedicated for TA applications, typically with extra gain as compared to US amplifier and high-input impedance value for broadband applications. TA preamplifier is the only preamplifier discussed in this patent and might be called preamplifier.
Transmission line is a single-ended electric wiring for AC (alternating current) signal with a specific impedance.
Tx—transmit mode.
US—ultrasound.
US mode—ultrasound mode with US Tx and US Rx regimes.
USTA—ultrasound and thermoacoustic.

Common Units of Measurements:
Hz—Hertz
kHz—kiloHertz
MHz—MegaHertz
µs—microsecond In an embodiment, the presently disclosed system and method provides a new serial architecture of a USTA system. Essentially the same analog and digital signal path is used for both US and TA modalities. All design modules are arranged in series along the signal path starting from the transducer array cable connector, as shown in FIG. 1. The modules which are not used in a particular operation mode are bypassed, i.e., excluded from the analog signal path. The HV pulser is bypassed by its internal switches in TA and US Rx modes. TA preamplifiers are disabled and bypassed in US modes. The serial architecture allows the instrument to maintain the best performance for each modality of a USTA system as well as to reduce component count, system size and cost. Performance of a serial USTA system in US modality is equivalent to the performance of a US system without a TA modality. Performance of the serial USTA system in TA modality is equivalent to the performance of a TA system without US modality, but in some cases the input impedance might be limited by high-voltage bleed resistor value. In an embodiment, the size and the number of components for a serial USTA system with custom TA preamplifier and switch IC is only marginally higher vs. the size and the number of components of the equivalent US system without dedicated TA abilities. Beamformer and HV circuitry, including pulser and HV power, are used in US mode only. In an embodiment, the TA preamplifier is used in TA mode only. All other components, including transducer array, AFE (ADC), FPGA, PC interface and software are used in both modes. Reduced component counts enable increased number of parallel channels per DAQ PCB.

Note that some US systems have a so-called Rx-only mode and reuse AFE/ADC, FGPA, and PC interface for both modalities. One example of such a system is the Vantage™ system available from Verasonics, Inc. of Kirkland, WA. Such systems, however, cannot be considered dual modality USTA systems with a serial design because they are lacking a dedicated TA preamplifier with high input impedance and extra gain required to archive broad signal bandwidth, high sensitivity, and low signal-to-noise ratio in TA mode. The TA mode of such a system provides poor image quality and is generally equivalent to US Rx mode. US systems with Rx-only mode might be upgraded for TA applications using an external TA preamplifier, for example the Legion preamplifier available from PhotoSound Technologies, Inc. of Houston, TX, but such upgrade is lacking HV switches, such as those shown in FIG. 1C-1E. An ultrasound system with such external TA preamplifier cannot be used in US mode without physical removal of the TA preamplifier.

Serial dual modality USTA architecture uses the same transducer array elements (101) and the same analog signal path from transducer element to AFE chip (110). Switching between US and TA modes is performed using switches as described in FIG. 1. Digital control over switch states is not shown, but control sequence and time diagrams are described in FIG. 2.

FIG. 1: US mode employs HV pulser, beamformer, and HV protection switches, which might be integrated inside a single pulser-beamformer IC (labeled as (102) in FIG. 1A-1E), for example Texas Instruments TX7332 or TX7316. The internal structure of the pulser block (102) is not shown. HV circuitry is disabled in TA and US Rx modes.

TA mode works with much weaker signals and much broader BW than US Rx mode. TA mode requires an extra amplification stage implemented as TA preamplifier (104), which might have high impedance input, programmable frequency filters and other features not required in US mode. In US mode TA preamplifier output should be disconnected and TA preamplifier bypassed, i.e. preamplifier input should be directly connected to the next stage of the analog signal chain instead of TA preamplifier output. Bypass connection and output connection might be controlled by two SPST switches (105), (106) (FIG. 1A) or one SPDT switch (107) (FIG. 1B) per analog channel to select TA or US modes. The state of TA preamplifier (103) switches is shown in FIG. 1A-1E for TA (Rx) mode and US (Rx and Tx) modes. All TA preamplifier switches in FIG. 1C-1E must be HV tolerant for operation in US Rx mode.

TA preamplifier might be implemented using discrete components or as an IC. TA preamplifier might have a single analog channel or multiple analog channels. TA preamplifier IC might have the switches (105)-(109) integrated or the switches (105)-(109) might be implemented as separate components.

Figure 1A:
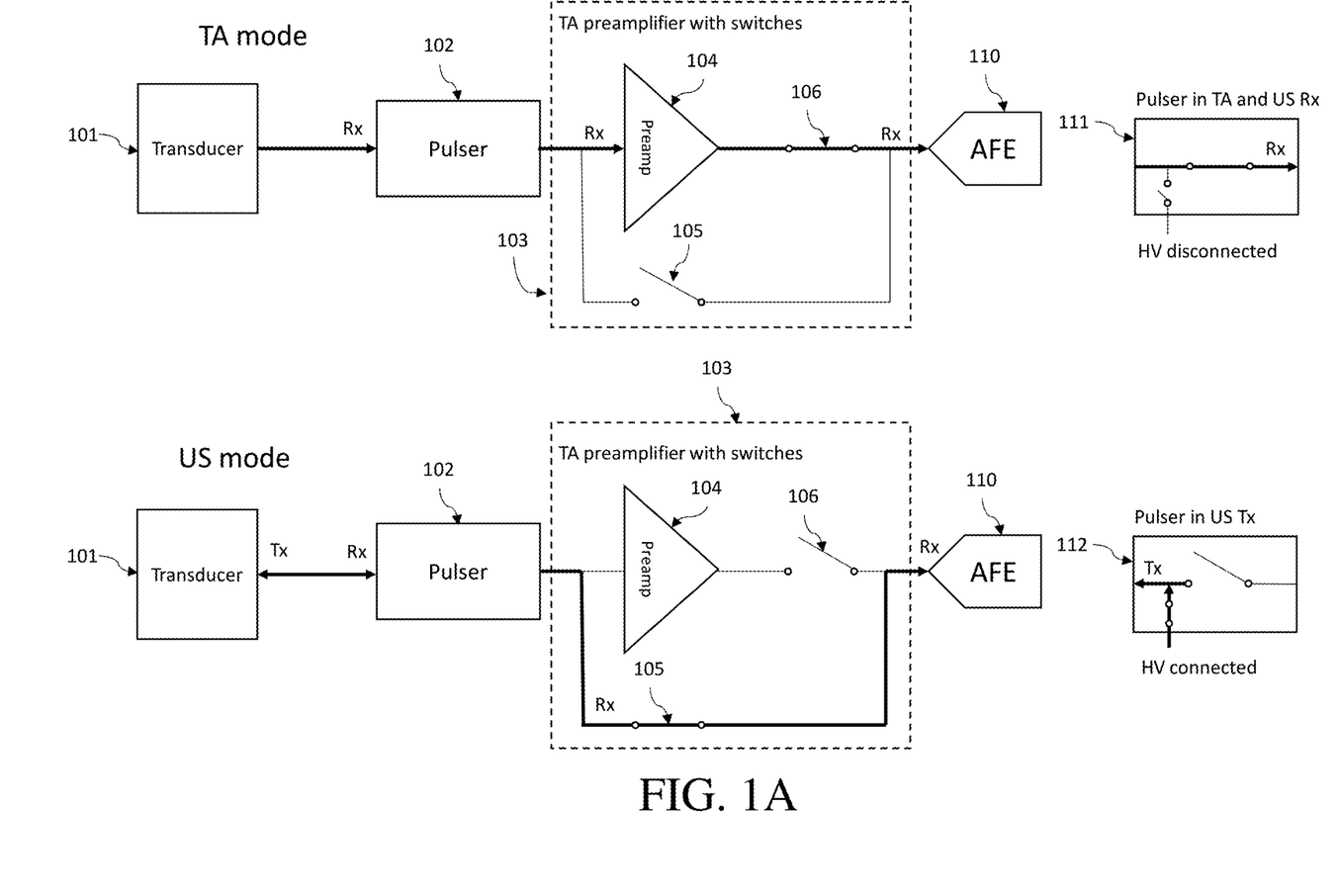
FIGS. 1A-1E show different embodiments of the TA preamplifier and its positions in the analog signal chain. The analog signal chain components are shown as geometric figures labeled from 101 to 110.

In TA and US Rx modes the pulser HV signal is disconnected from the analog signal chain and the pulser allows the signal through, as shown in (111).

Tx signal is a HV signal present in US mode only. Tx signal is temporally separated from Rx signal in US mode. HV Tx signal propagates from the pulser (102) into the transducer and not present on the low-voltage analog output from the pulser to AFE side as shown in (112).

Signal acquisition in TA applications has a low duty cycle, i.e. a fraction of time during which preamplifier operates while receiving input TA signals (202) (FIG. 2A) relative to the time when TA preamplifier operation is not required. Fast disabling and enabling DAQ electronics including TA preamplifier, the second stage amplifier and ADC enables significant power saving and reduction of average power consumption. The time with enabled TA preamplifier (full power mode) is shown as (204) and the time with disabled TA preamplifier is shown as (203) and (205) in FIG. 2A.

Figure 1B:
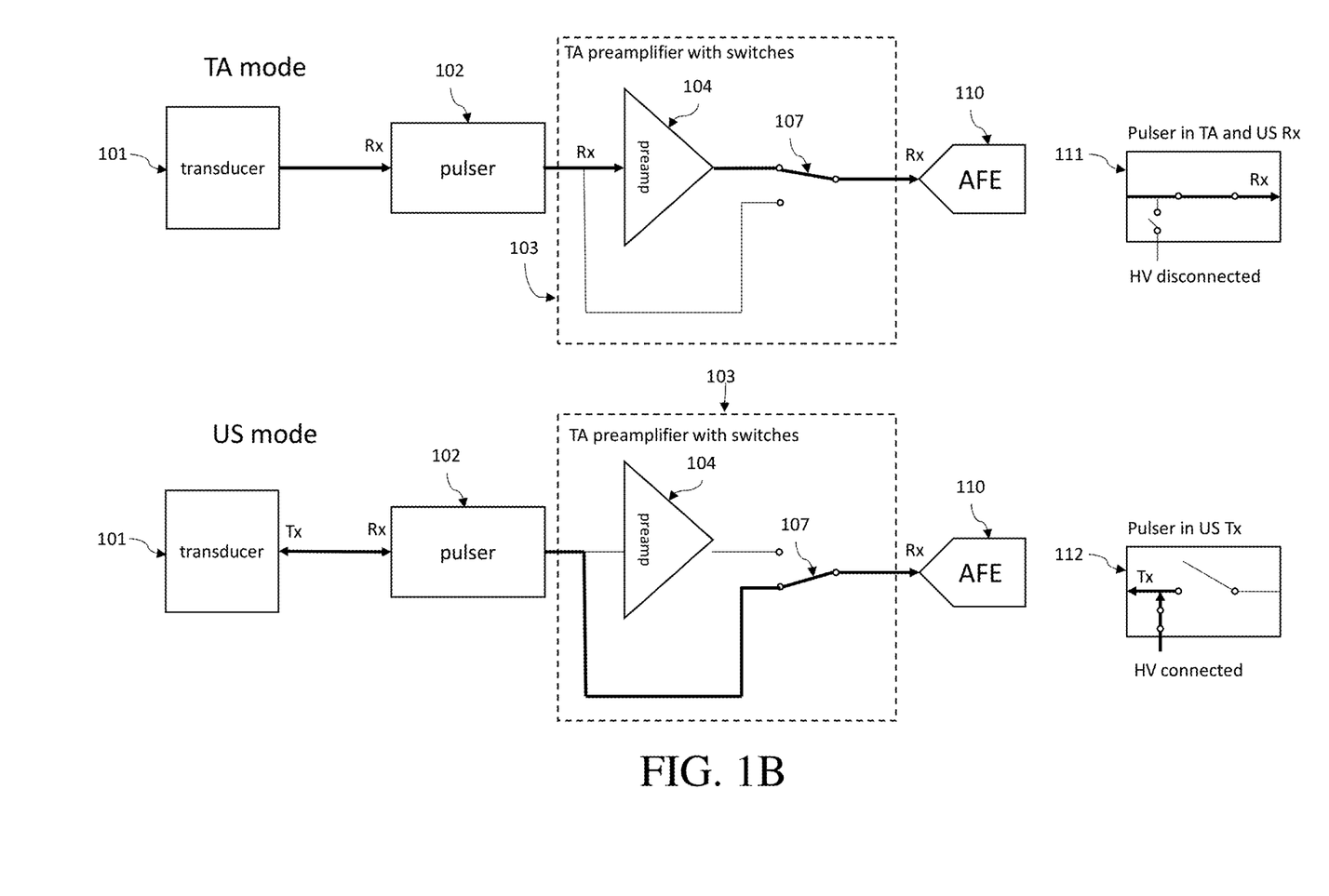

FIGS. 1A and 1B describe applications with TA preamplifier located in LV part of the circuit. TA preamplifier in LV part of the circuit can be equipped with LV switches. FIGS. 1A and 1B have TA preamplifier with two SPST switches per channel and one SPDT switch per channel accordingly.

FIG. 1A shows an analog signal path implementation with two SPST switches per channel. Each SPST switch has an open and a closed position. One switch is a bypass switch (105), and the other is an output switch (106). In the TA mode the output switch (106) is closed to deliver preamplifier output signal to AFE (110); the bypass switch (105) is open. In US mode the output switch (106) is open and used to exclude TA preamplifier from the signal path; the bypass switch (105) is closed and is used to pass analog signal to AFE (110).

FIG. 1B shows an analog signal path implementation with one SPDT switch per channel. The SPDT switch (107) has preamplifier output position (used in TA mode) and preamplifier bypass position (used in US mode).

Figure 1C:
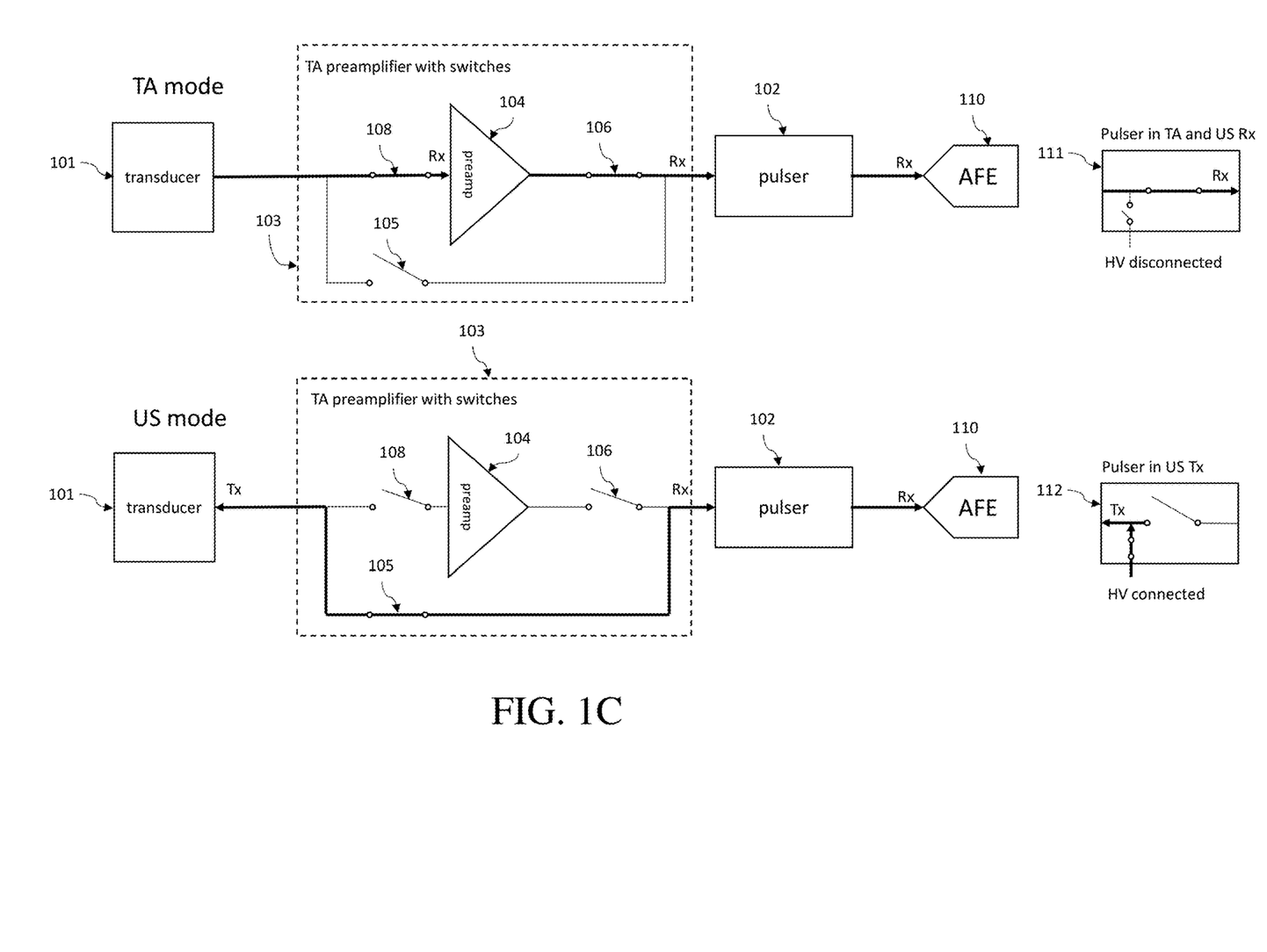
Figure 1D:
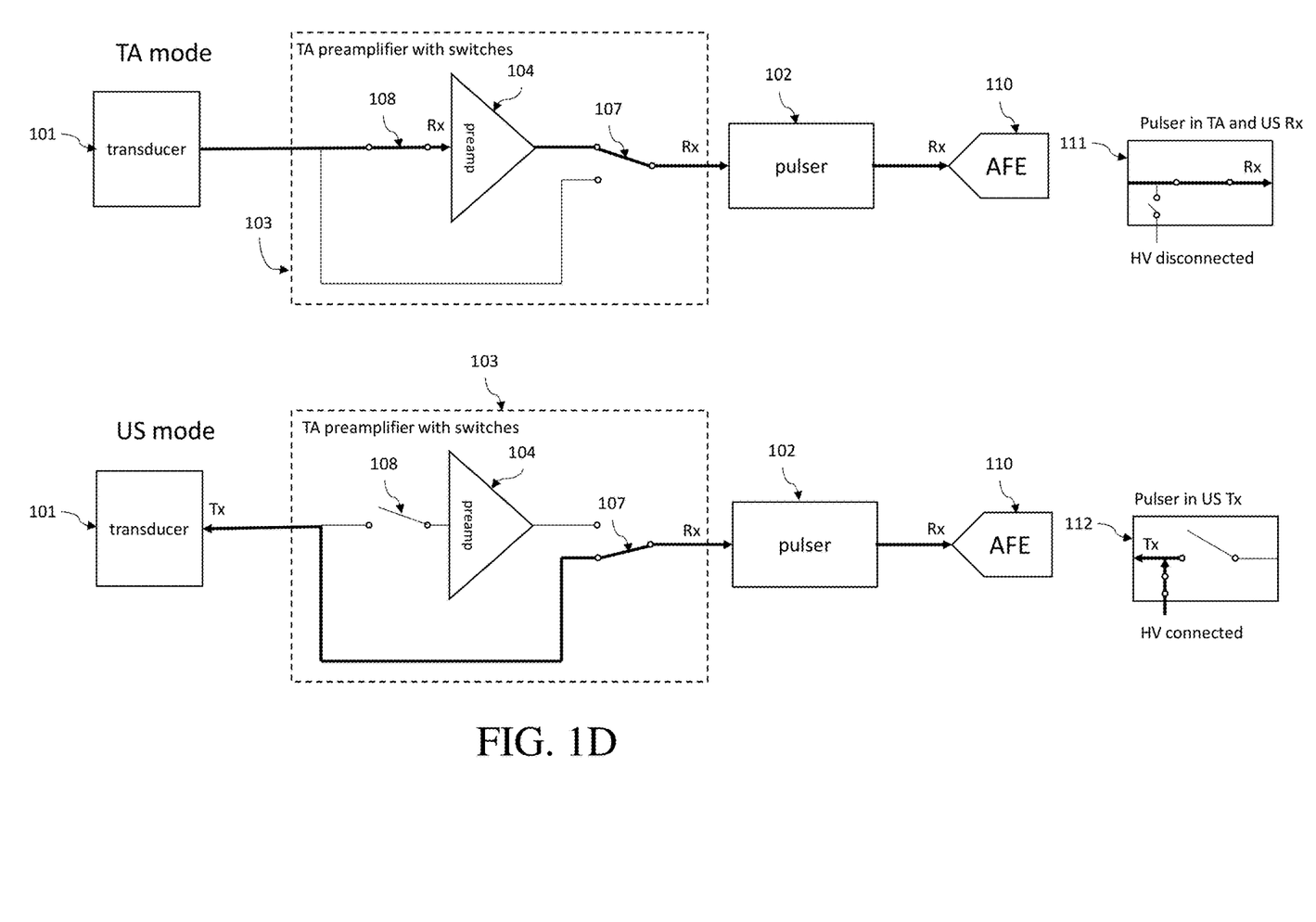
Figure 1E:
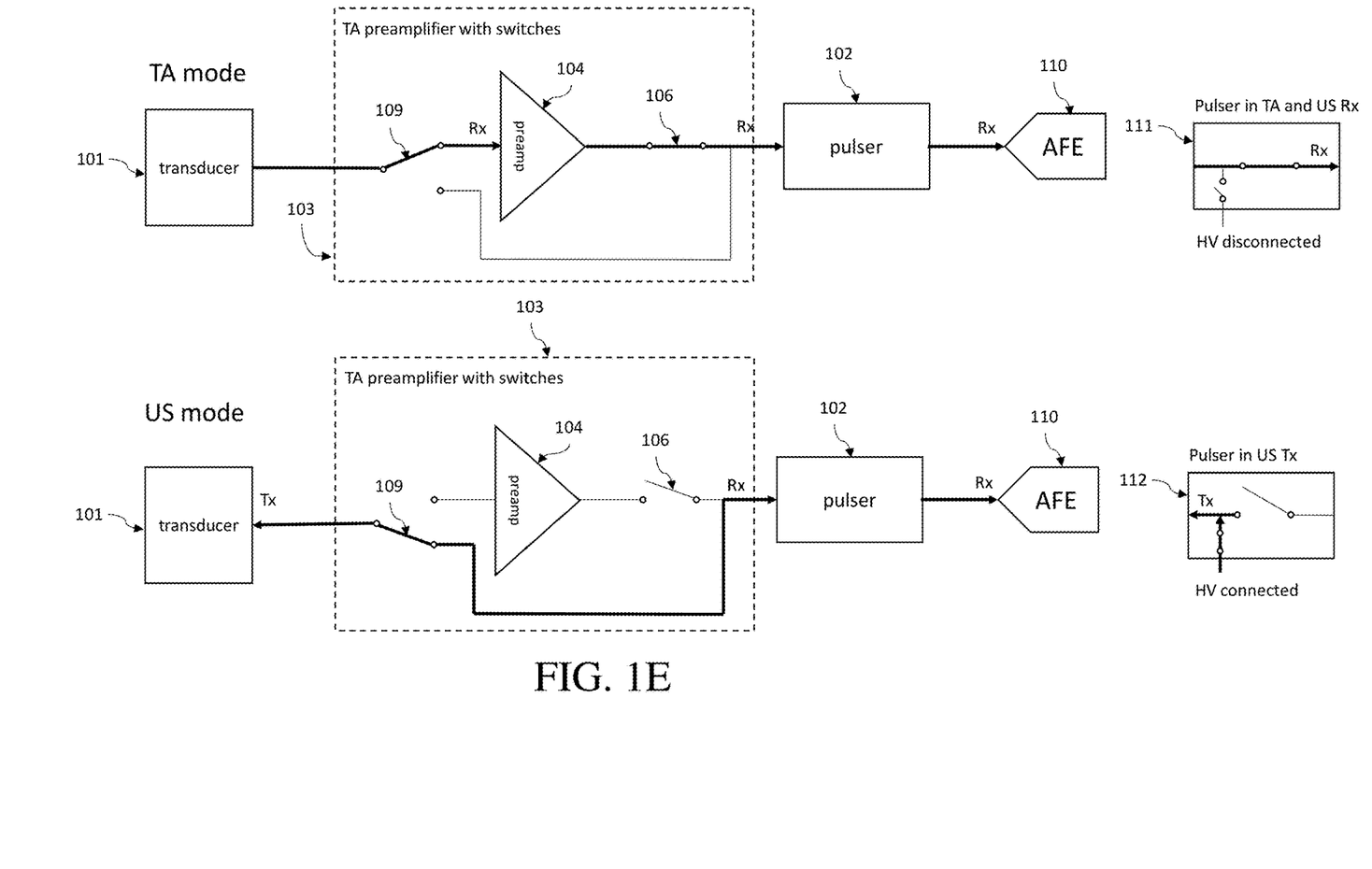

If the TA preamplifier (104) is equipped with HV switches it can be placed right after the transducer (101) into the analog signal chain as shown in FIG. 1C-1E. Such placement of TA preamplifier allows its integration into transducer array housing, which improves TA signal sensitivity, EMI rejection and quality, especially in case of low capacitance or high-frequency TA transducers. It enables a driving transmission line directly out of the transducer array housing. Such architecture allows use of long transducer array cables without sacrificing TA mode performance for any cable length. The pulser and subsequent components can be placed on the other end of micro-coaxial cable bundle inside USTA device housing.

An extra HV protection switch (108) (FIG. 1C, 1D) or (109) (FIG. 1E) is required to protect the preamplifier input from HV in US Tx mode. HV switches can be arranged as three SPST switches (105), (106), and (108) in FIG. 1C or as one SPDT and one SPST switches in FIG. 1D, 1E. The only SPST can be used as TA preamplifier input switch (108) (FIG. 1D) or output switch (106) (FIG. 1E).

FIG. 1C-1E describe configurations with TA preamplifier located in HV part of the circuit. TA preamplifier located in HV part of the circuit must be equipped with HV switches for HV protection. In US Tx mode, TA preamplifier input and output must be disconnected from the analog signal chain, which requires an extra switch for preamplifier input. FIG. 1C describes TA preamplifier with HV SPST switches. FIGS. 1D and 1E, TA preamplifier with HV SPST and SPDT switches.

FIG. 1C shows an analog signal path implementation with three HV tolerant SPST switches per channel. One switch is a bypass switch (105), and another is an output switch (106), the third switch is the input protection switch (108). In TA mode the input switch (108) is closed to allow transmission of the signal from the transducer to the preamplifier input; the output switch (106) is closed to allow transmission of the signal from the preamplifier output through the pulser (102) to AFE (110); the bypass switch (105) is open. In US mode the input and output switches (108) and (106), respectively, are open to exclude TA preamplifier from the analog signal path and to protect preamplifier from HV US Tx signal; the bypass switch (105) is closed and used to pass analog Rx signal through pulser state (111) to AFE (110) or Tx signal from the pulser to the transducer.

FIGS. 1D and 1E show an analog signal path implementation with one HV tolerant SPST switch and one HV tolerant SPDT switch per channel.

In FIG. 1D, SPDT switch (107) replaces two SPST switches (105) and (106) (FIG. 1C).

In FIG. 1E, SPDT switch (109) replaces two SPST switches (105) and (108) (FIG. 1C).

Figure 1F:
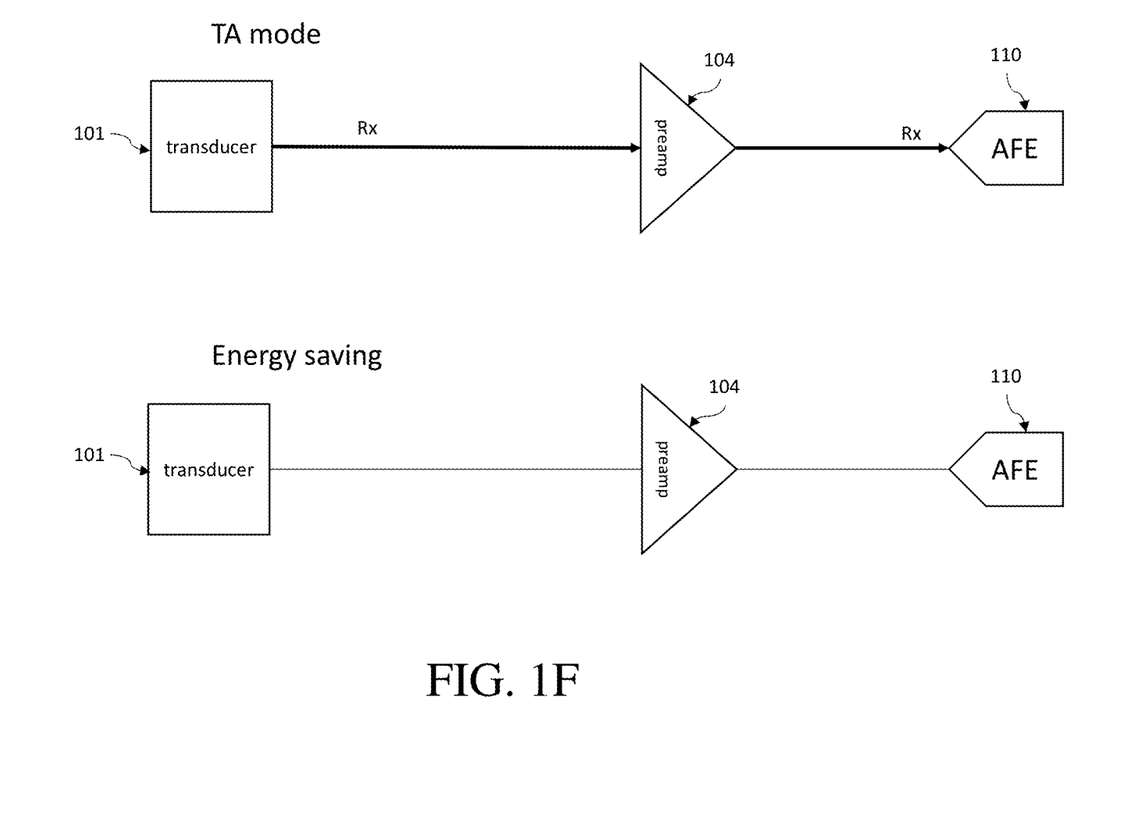
FIG. 1F describes a system with TA only mode.

FIG. 1F describes a system with TA only mode. The top panel describes Rx TA operation. The bottom panel describes energy saving state with TA preamplifier (104) in a standby mode. The switches are not shown in FIG. 1F, but might be present. If switches are present, they must operate in TA mode as described in the top panels of FIG. 1A-1E.

Figure 2A:
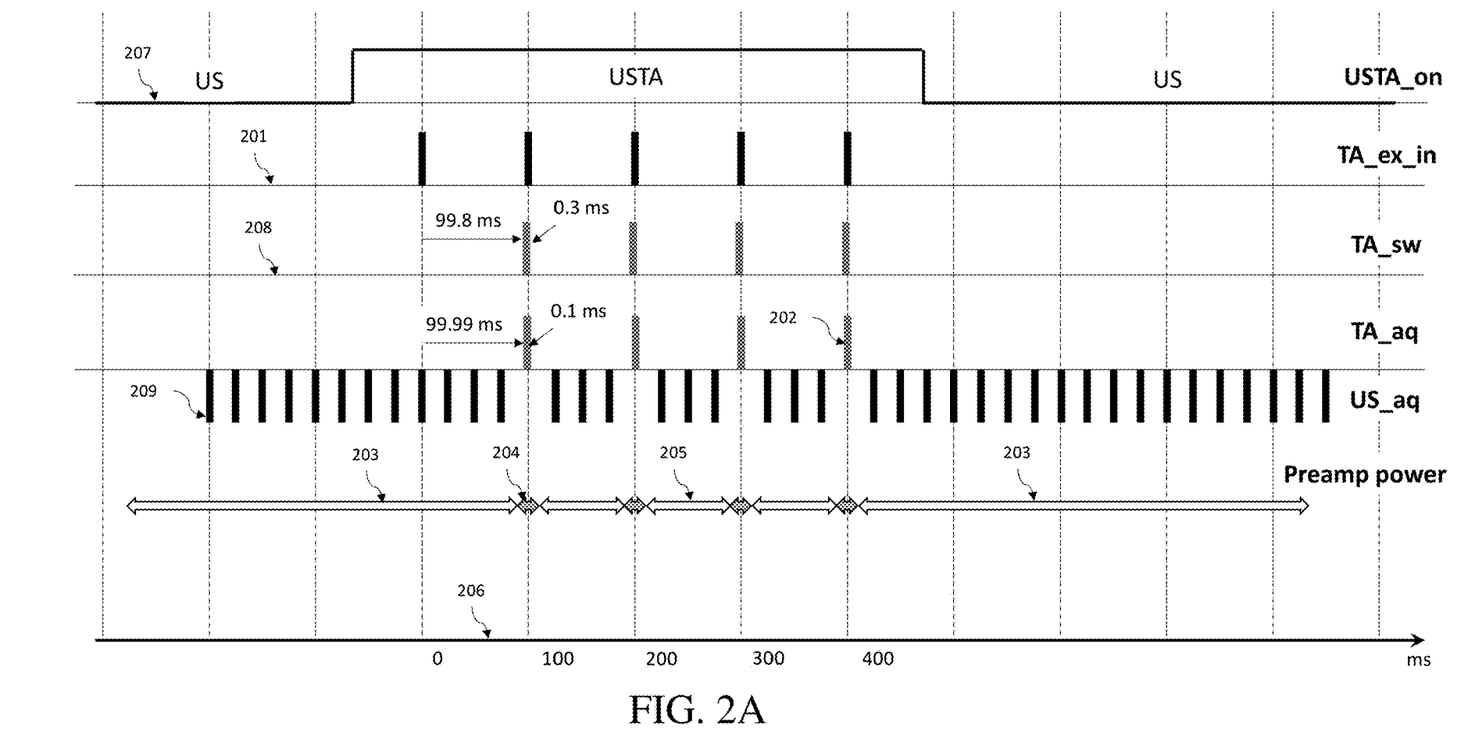
FIG. 2A shows an example of the timing diagram and the energy-saving protocol for a USTA system with a 40 Hz US component and a 10 Hz TA component. (207)—control US/USTA signal; (201)—10 Hz trigger signal of TA excitation; (202)—10 Hz TA acquisition triggered with a 99.99 ms delay with respect to (201); (208)—10 Hz TA switch activation signal, delayed by 99.8 ms with respect to (201); (209)—40 Hz US acquisition signal; (203)-(205) are segments of high (204) and standby (203) and (205) power modes of the TA preamplifier; (206)—time axis in milliseconds.

FIG. 2A displays a time diagram for a USTA system with implemented fast energy saving technology. The dual modality USTA mode is activated for a limited time corresponding to the high USTA_on signal on the time line (207). TA_ex_in signals on the time line (201) indicate TA excitation events, for example, firing of the excitation laser in the case of photoacoustic imaging.

TA_aq signals (202) indicate TA data acquisition events, which typically last no longer than 100-200 μs and are offset by a fixed delay from the preceding TA excitation signal. The time intervals (203)-(205) represent TA preamplifier power modes. TA preamplifier power can be disabled before and after activation of USTA mode (see time line (207)) as indicated by time intervals (203) and in the pauses between TA data acquisition events (202), as indicated by the time intervals (205), which can be used for acquisition of US frames (209).

The time intervals (203) and (205) indicate a fast power saving mode of TA preamplifier. The time intervals (204) indicate a full power mode of TA preamplifier including two transient stages of <100 μs each, when TA preamplifier is being turned on or turned off. In the example shown in FIG. 2A, the TA preamplifier stays in the power saving mode for ≥99% of time and is active for only ≤1% of time considering a conventional 10 Hz TA excitation rate. The time line (208) shows TA_sw signals with high values used to enable series connection for the TA preamplifier used for the TA mode. TA_sw low values are used to enable bypass connection for the TA preamplifier used for the US mode.

Figure 2B:
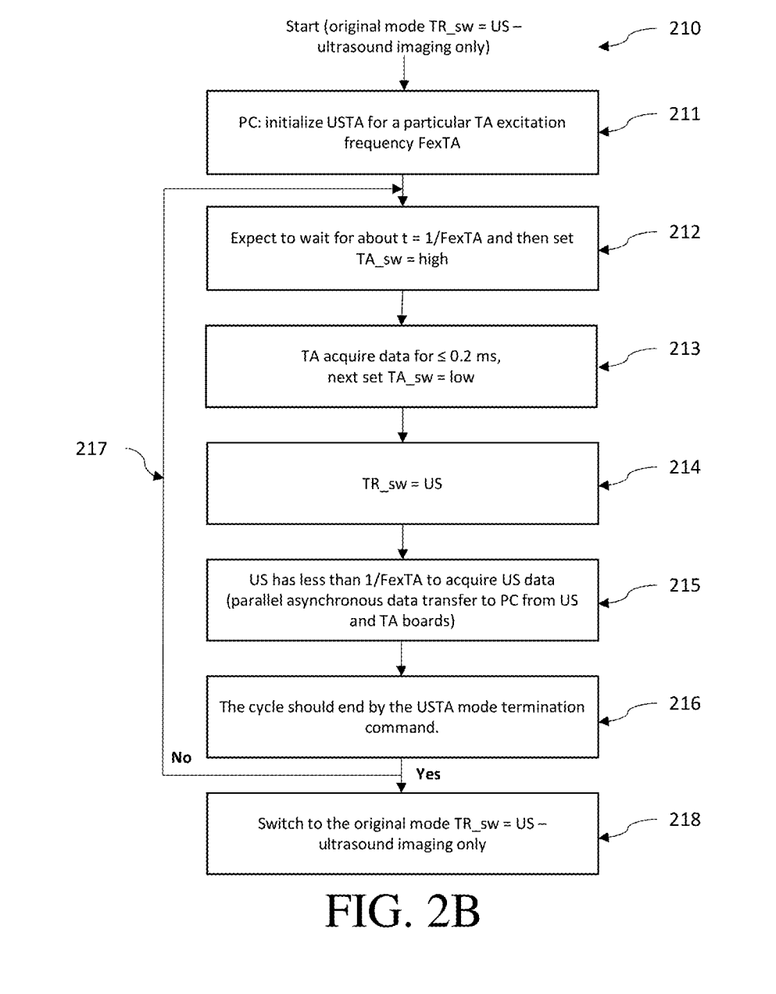
FIG. 2B shows an embodiment of a USTA imaging operation sequence with interleaving US and TA image frames.

FIG. 2B shows an operational sequence for a USTA imaging system with implemented fast energy saving technology. The USTA imaging system is normally operated in US mode (210) very much like its cousin—clinical ultrasound. When there is a requirement to enable a USTA imaging, the system is getting initialized for a particular TA excitation frequency FexTA (211), corresponding, for example, to the onset of the high USTA_on signal (time line (207), FIG. 2A). The system then continues US imaging and waits for the first TA_ex_in signal (time line (201), FIG. 2A) to arrive. The controller switches on power in the TA preamplifiers and enables TA acquisition event ((202) in FIG. 2A) with a time delay slightly shorter than 1/FexTA (time line (208), FIG. 2A). Subsequently, the system reactivates US imaging (214) until the next TA_sw signal is received (line (208), FIG. 2A). Such sequence of interleaving TA and US imaging events continues until a USTA mode termination command arrives, for example in a form of a low-level USTA_on signal (time line (207), FIG. 2A) at which point the system returns to its default US imaging mode.

The ability to switch to low power mode when not performing thermoacoustic receive operations allows substantial reduction in power requirements. Among the advantages of such reduction are the ability to include the TA preamplifier, DAQ, analog-to-digital converter or ultrasound analog front-end within a housing of a probe or transducer array.

At least some aspects disclosed can be embodied, at least in part, in software. That is, the techniques may be carried out in a special purpose or general purpose computer system or other data processing system in response to its hard-core or soft-core processor, such as a microprocessor, executing sequences of instructions contained in a memory, such as ROM, volatile RAM, non-volatile memory, cache or a remote storage device. Functions expressed in the claims may be performed by a processor in combination with memory storing code and should not be interpreted as means-plus-function limitations.

Routines executed to implement the embodiments may be implemented as part of an application, operating system, firmware, ROM, middleware, service delivery platform, SDK (Software Development Kit) component, web services, or other specific application, component, program, object, module or sequence of instructions referred to as "computer programs." Invocation interfaces to these routines can be exposed to a software development community as an API (Application Programming Interface). The computer programs typically comprise one or more instructions set at various times in various memory and storage devices in a computer, and that, when read and executed by one or more processors in a computer, cause the computer to perform operations necessary to execute elements involving the various aspects.

A machine-readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer-to-peer networks. Different portions of the data and instructions can be obtained from different centralized servers and/or peer-to-peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine-readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others.

In general, a machine-readable medium includes any mechanism that provides (e.g., stores) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

What is claimed is:

1. An instrument for thermoacoustic data acquisition and/or imaging, comprising:
    a transducer or a transducer array for receiving thermoacoustic signals from an interrogated object;
    a thermoacoustic data acquisition unit comprising a thermoacoustic preamplifier and an analog front end for providing analog to digital conversion of input signals, said data acquisition unit or one or more of its individual components having a fast-disable low power mode and a fast-enable full power mode, each mode being capable of being activated multiple times per second between and during measurement cycles;
    wherein the thermoacoustic data acquisition unit is configured to amplify and digitize signals received by said transducer or said transducer array;
    a circuit providing digital processing and/or digital control in the instrument;
    wherein the instrument is configured to switch said thermoacoustic data acquisition unit or one or more of its components between the fast-disable low power mode and the fast-enable full power mode according to a preset protocol;
    wherein the instrument is configured to reduce thermoacoustic preamplifier power consumption many times by keeping the thermoacoustic preamplifier in the fast-disable low power mode for ≥99% of the time during a thermoacoustic measurement cycle.

2. The instrument according to claim 1 wherein the circuit providing digital processing and/or digital control is a field programmable gate array.

3. The instrument according to claim 1, wherein the instrument is configured to switch said thermoacoustic data acquisition unit or one or more of its components into said full power mode when said instrument is acquiring the thermoacoustic signals and into said fast-disable low power mode when said instrument is not acquiring thermoacoustic signals.

4. The instrument according to claim 1, wherein the thermoacoustic preamplifier of said thermoacoustic data acquisition unit is placed within a housing incorporating said transducer or said transducer array.

5. The instrument according to claim 1, wherein one or more of the instrument's components are integrated into a portable and/or battery-operated device.

6. The instrument according to claim 1, wherein one or more of the instrument's components are integrated into a handheld device.

7. The instrument according to claim 1, wherein:
    the transducer or transducer array comprises one or more transducers configured for applying mechanical energy to the interrogated object and receiving acoustic signals from the interrogated object;
    a pulser is provided for applying non-stationary electromagnetic energy to said transducer or said transducer array enabling the instrument's operation ion ultrasound emit mode;
    wherein the instrument is configured with a plurality of electronic switches used to bypass the thermoacoustic preamplifier in an analog signal chain in ultrasound mode and enable the thermoacoustic preamplifier in thermoacoustic mode, the plurality of electronic switches comprising at least two single-pole-single-throw (SPST) switches or at least one single-pole-double-throw (SPDT) switch per channel, the plurality of electronic switches being configured to select thermoacoustic or ultrasound modes, the plurality of electronic switches being configured such that at least one of said plurality of electronic SPST switches or SPDT switch position is a bypass switch and another of said plurality of electronic SPST switches or SPDT switch position is an output switch.

8. The instrument according to claim 7 wherein the circuit providing digital processing and/or digital control is a field programmable gate array.

9. The instrument according to claim 7, configured such that the same transducer elements and analog front-end channels are used in both ultrasound and thermoacoustic modalities.

10. The instrument according to claim 7, wherein the instrument is configured to switch said thermoacoustic preamplifier into said fast-enable full power mode when said instrument is acquiring the acoustic signals and into said fast-disable low power mode when said instrument is not acquiring the acoustic signals.

11. The instrument according to claim 7, wherein said pulser and/or thermoacoustic preamplifier are placed within a housing incorporating said transducer or said transducer array.

12. The instrument according to claim 7, wherein one or more of the instrument's components are integrated into a portable and/or battery-operated device.

13. The instrument according to claim 7, wherein all or some of the instrument's components are integrated into a handheld device.

14. The instrument according to claim 7, wherein the instrument is configured to use a plurality of pulser-voltage protection switches and bypass switches.

15. The instrument according to claim 14, wherein the plurality of pulser-voltage protection switches and bypass switches are integrated inside a pulser circuit.

16. The instrument according to claim 7, wherein the instrument is configured such that when the instrument operates in ultrasound receive mode or thermoacoustic mode, the pulser is idle allowing received signals through while having said pulser disconnected from an analog signal path using said pulser-voltage protection switches; and when the instrument operates in ultrasound transmit mode, the pulser is actively applying electromagnetic energy to said transducer or said transducer array through said pulser-voltage protections switches, and is disconnected form the thermoacoustic preamplifier and the analog front end.

* * * * *